(12) United States Patent
Sakai et al.

(10) Patent No.: US 8,283,468 B2
(45) Date of Patent: Oct. 9, 2012

(54) ORGANOMETALLIC COMPLEX AND METHOD FOR PRODUCING THE SAME

(75) Inventors: Hiroshi Sakai, Wako (JP); Izuru Kanoya, Wako (JP); Terumi Furuta, Wako (JP); Mitsuya Hosoe, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 238 days.

(21) Appl. No.: 12/879,068

(22) Filed: Sep. 10, 2010

(65) Prior Publication Data

US 2011/0065921 A1     Mar. 17, 2011

(30) Foreign Application Priority Data

Sep. 15, 2009   (JP) .................................. 2009-213416

(51) Int. Cl.
    *C07D 213/80*     (2006.01)
    *C07F 1/08*     (2006.01)
(52) U.S. Cl. .......................................................... 546/5
(58) Field of Classification Search ........................ 546/5
    See application file for complete search history.

(56) References Cited

OTHER PUBLICATIONS

Panella et al. "Hydrogen Adsorption in Metal-Organic Frameworks: Cu-MOFs and Zn-MOFs Compared" Advanced Functional Materials, 2006, vol. 16, pp. 520-524.*
Panella, B., Hirscher, M., Putter, H., and Muller, U., Hydrogen Adsorption in Metal-Organic Frameworks: Cu-MOFs and Zn-MOFs Compared, Advanced Functional Materials, Mar. 2006, p. 520-524, vol. 16, Issue 4, Wiley-VCH, Weinheim, Germany.

* cited by examiner

*Primary Examiner* — Joseph Kosack
(74) *Attorney, Agent, or Firm* — Capitol City TechLaw, PLLC

(57) ABSTRACT

An organometallic complex $[Cu_2(pyridine-3,5-dicarboxylate)_2]_n$ is provided by bonding a plurality of $Cu_2(pyridine-3,5-dicarboxylate)_2$ repeating units to each other. The organometallic complex can be obtained by the steps of dissolving copper acetate monohydrate or anhydrate and pyridine-3,5-dicarboxylic acid in a solvent, heating the solution at 50° C. to 140° C. for 24 to 168 hours to generate a reaction product, and then removing a guest molecule from the reaction product.

14 Claims, 13 Drawing Sheets

PYRIDINE-3, 5-DICARBOXYLATE

FIG. 3
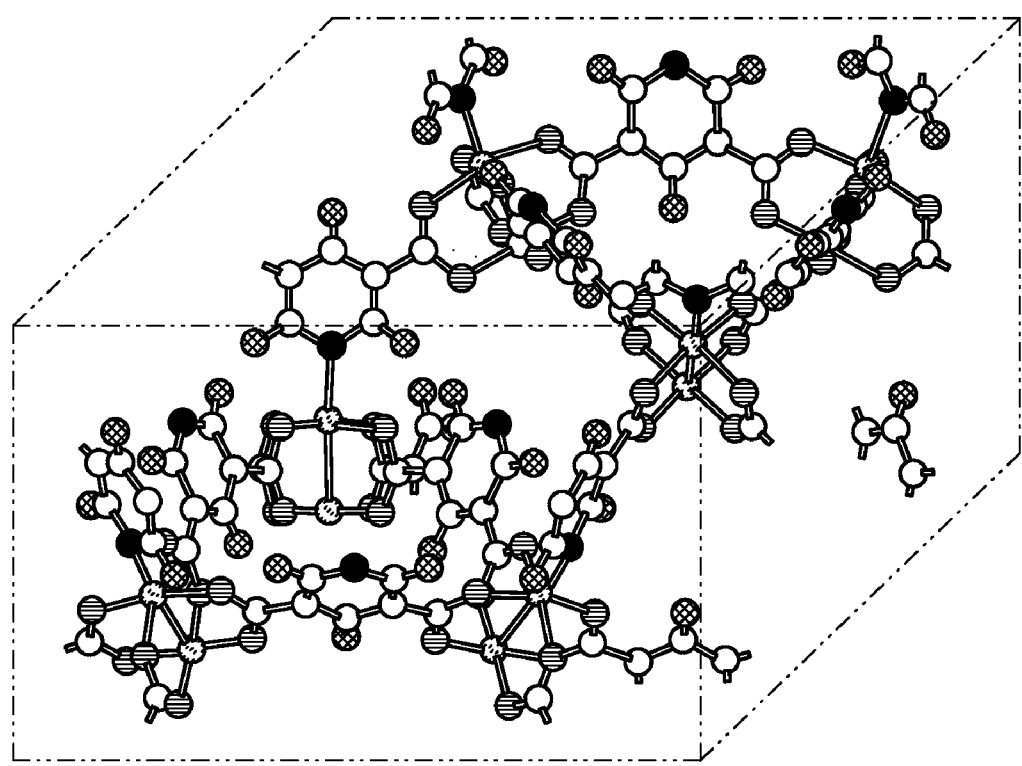
H
C
N
O
Cu
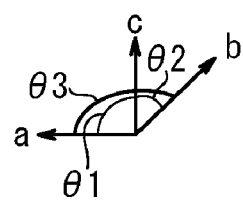
$\theta1 = \theta2 = 90°$
$\theta3 = 120°$ $\theta 3 = 120°$

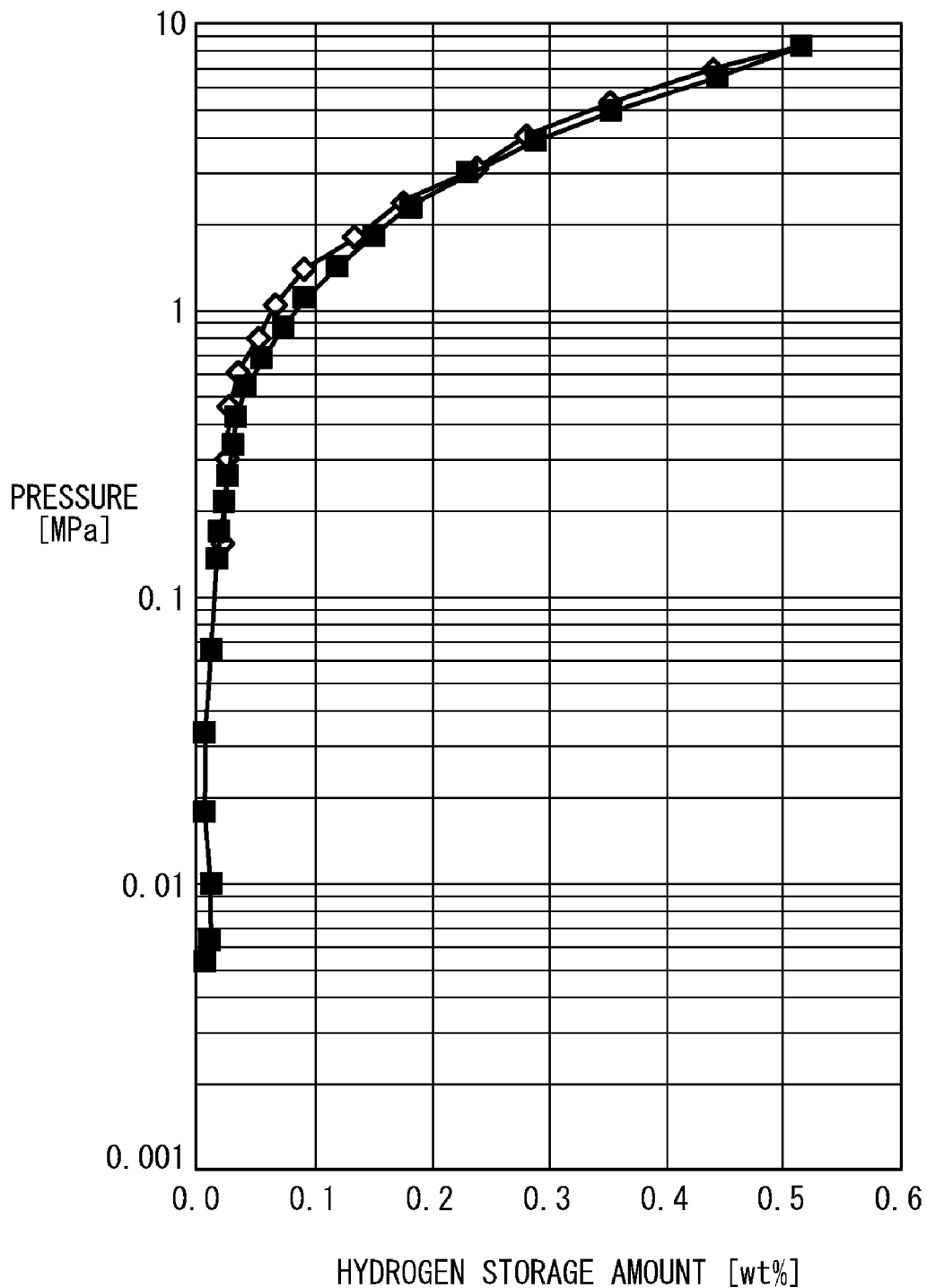

ORGANOMETALLIC COMPLEX AND METHOD FOR PRODUCING THE SAME

CROSS-REFERENCE TO RELATED APPLICATION

This application is based upon and claims the benefit of priority from Japanese Patent Application No. 2009-213416 filed on Sep. 15, 2009, of which the contents are incorporated herein by reference.

BACKGROUND OF THE INVENTION

1. Field of the Invention

The present invention relates to an organometallic complex usable as a hydrogen storage material or the like and a method for producing the same.

2. Description of the Related Art

As is known in the art, fuel cells generate electricity using a fuel gas such as hydrogen gas supplied to an anode and an oxidant gas such as oxygen gas supplied to a cathode. Therefore, for example, a fuel-cell car containing the fuel cell is equipped with a gas storage vessel for storing the hydrogen gas. The fuel-cell car is driven by utilizing the air as an oxygen-containing gas and the hydrogen gas supplied from the vessel as reactant gases.

As is clear from the above, as the gas storage vessel has a higher hydrogen storage capacity, the fuel-cell car can be driven over a longer distance. However, when the fuel-cell car is equipped with an excessively large gas storage vessel, the fuel-cell car has an increased weight, resulting in a high load on the fuel cell disadvantageously. From this viewpoint, various studies have been made on a gas storage vessel having a high hydrogen storage capacity with a small volume.

In one attempt, a material for storing or adsorbing hydrogen (hereinafter referred to as a hydrogen storage material) such as a hydrogen storage alloy is placed inside the gas storage vessel. The hydrogen storage material is capable of incorporating hydrogen into its molecular structure, so that a larger amount of hydrogen can be stored in the vessel as compared with the vessel volume.

An organometallic complex is known as a preferred hydrogen storage material. The organometallic complex is a compound containing a metal core and an organic group bonded thereto.

In the organometallic complex, the organic group is bonded to the metal core in a regular manner. Therefore, pores having relatively uniform diameters may be formed in its molecular structure. An inner wall of each pore may act as a site for physically adsorbing hydrogen. Of course, it is preferred that the complex has a higher hydrogen storage capacity.

B. Panella, M. Hirscher, H. Putter, and U. Muller have reported hydrogen adsorption properties of $[Cu_3(benzene-1,3,5-tricarboxylate)_2(H_2O)_3]_n$ (hereinafter referred to as the Cu-BTC) at various temperatures in *Advanced Functional Materials*, 16(4), 520-524 (March 2006), "*Hydrogen Adsorption in Metal-Organic Frameworks: Cu-MOFs and Zn-MOFs Compared*". According to this report, the hydrogen adsorption amount of the complex is 3.6% by weight at 77 K (pressure extrapolation value), and is 0.35% at the room temperature 298 K under a hydrogen pressure of 65 bar (6.5 MPa). Thus, the hydrogen adsorption amount is less than 0.4% by weight at the room temperature.

However, the fuel-cell car is generally driven at an environmental temperature around the room temperature, so that it is preferred that the hydrogen storage material of the organometallic complex exhibits a larger hydrogen adsorption/release amount around the room temperature.

SUMMARY OF THE INVENTION

A general object of the present invention is to provide an organometallic complex having a relatively large hydrogen adsorption/release amount around room temperature.

A principal object of the present invention is to provide a method for producing such an organometallic complex.

According to an aspect of the present invention, there is provided an organometallic complex represented by the formula of $[Cu_2(pyridine-3,5-dicarboxylate)_2]_n$, comprising a plurality of $Cu_2(pyridine-3,5-dicarboxylate)_2$ repeating units bonded to each other.

The organometallic complex has a relatively high hydrogen storage capacity within a temperature range around room temperature. For example, when the organometallic complex is placed in a vessel, a large amount of hydrogen gas can be stored in the vessel.

Therefore, the hydrogen can be supplied from the vessel over a longer time, and a fuel cell or the like can be driven by the hydrogen over a longer time. Thus, in the operation of a fuel-cell car using the fuel cell, the hydrogen refueling frequency can be reduced. In other words, the fuel-cell car can be driven over a longer distance.

The organometallic complex generally has such a structure that four pyridine-3,5-dicarboxylate groups are coordinately bonded to one Cu dimer moiety (one Cu—Cu bond), and two adjacent Cu dimer moieties are bonded via one pyridine-3,5-dicarboxylate group.

The organometallic complex may be a layer compound formed by stacking two-dimensional structures comprising the $Cu_2(pyridine-3,5-dicarboxylate)_2$ repeating units two-dimensionally bonded to each other.

In this case, the organometallic complex has a unit cell containing twelve Cu atoms and twelve pyridine-3,5-dicarboxylate groups. The unit cell has a space group of $P6_3mc$ according to the Hermann-Mauguin notation. This means that the $[Cu_2(pyridine-3,5-dicarboxylate)_2]_n$ complex has a hexagonal crystal system.

The organometallic complex often has a cavity surrounded by a plurality of Cu dimer moieties and a plurality of pyridine-3,5-dicarboxylate groups. Though the opening diameter and inner diameter of the cavity are only several Angstroms (i.e. less than 10 Angstroms), the hydrogen molecules can be introduced into and released from the cavity having such sizes.

In this case, Cu, O, and N atoms are exposed to the cavity in the inner wall of the cavity. The atoms effectively act as hydrogen molecule adsorption sites.

For the above reasons, the organometallic complex can store and release a large amount of the hydrogen depending on the increase and decrease of ambient hydrogen pressure even at approximately room temperature.

According to another aspect of the present invention, there is provided a method for producing an organometallic complex represented by the formula of $[Cu_2(pyridine-3,5-dicarboxylate)_2]_n$, comprising a plurality of $Cu_2(pyridine-3,5-dicarboxylate)_2$ repeating units bonded to each other. The method comprises the steps of dissolving copper acetate monohydrate or copper acetate anhydrate and pyridine-3,5-dicarboxylic acid in a solvent to prepare a solution, heating the solution at 50° C. to 140° C. for 24 to 168 hours to obtain a reaction product from the copper acetate monohydrate or anhydrate and the pyridine-3,5-dicarboxylic acid, and removing a guest molecule from the reaction product.

The above described organometallic complex [Cu$_2$(pyridine-3,5-dicarboxylate)$_2$]$_n$, which has a high hydrogen storage capacity around room temperature, can be easily produced by the steps.

It is preferred that acetic acid or formic acid is added to the solution. In this case, the resultant [Cu$_2$(pyridine-3,5-dicarboxylate)$_2$]$_n$ has a high crystallinity. In other words, the [Cu$_2$(pyridine-3,5-dicarboxylate)$_2$]$_n$ can be easily produced with the high crystallinity by heating the solution after the addition of the acetic or formic acid.

Specifically, for example, the guest molecule may be removed from the reaction product by the steps of washing the reaction product with a solvent, replacing the solvent molecule contained in the washed reaction product with a dry chloroform molecule, and subjecting the reaction product to a heating treatment under a reduced pressure.

The above and other objects features and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIG. 3 is a schematic stereoscopic view showing a unit cell of a [Cu$_2$(pyridine-3,5-dicarboxylate)$_2$]$_n$ complex;

FIG. 13 is a graph showing the relation between the weight ratio of stored hydrogen to the crystals and the inner hydrogen pressure of a sample cell for a displacement-type hydrogen pressure-composition isothermal chart measurement apparatus.

DESCRIPTION OF THE PREFERRED EMBODIMENTS

A preferred embodiment of the organometallic complex and the production method of the present invention will be described in detail below with reference to the accompanying drawings.

The organometallic complex of this embodiment contains Cu$_2$(pyridine-3,5-dicarboxylate)$_2$ repeating units, and is represented by the formula of [Cu$_2$(pyridine-3,5-dicarboxylate)$_2$]$_n$.

Figure 1:
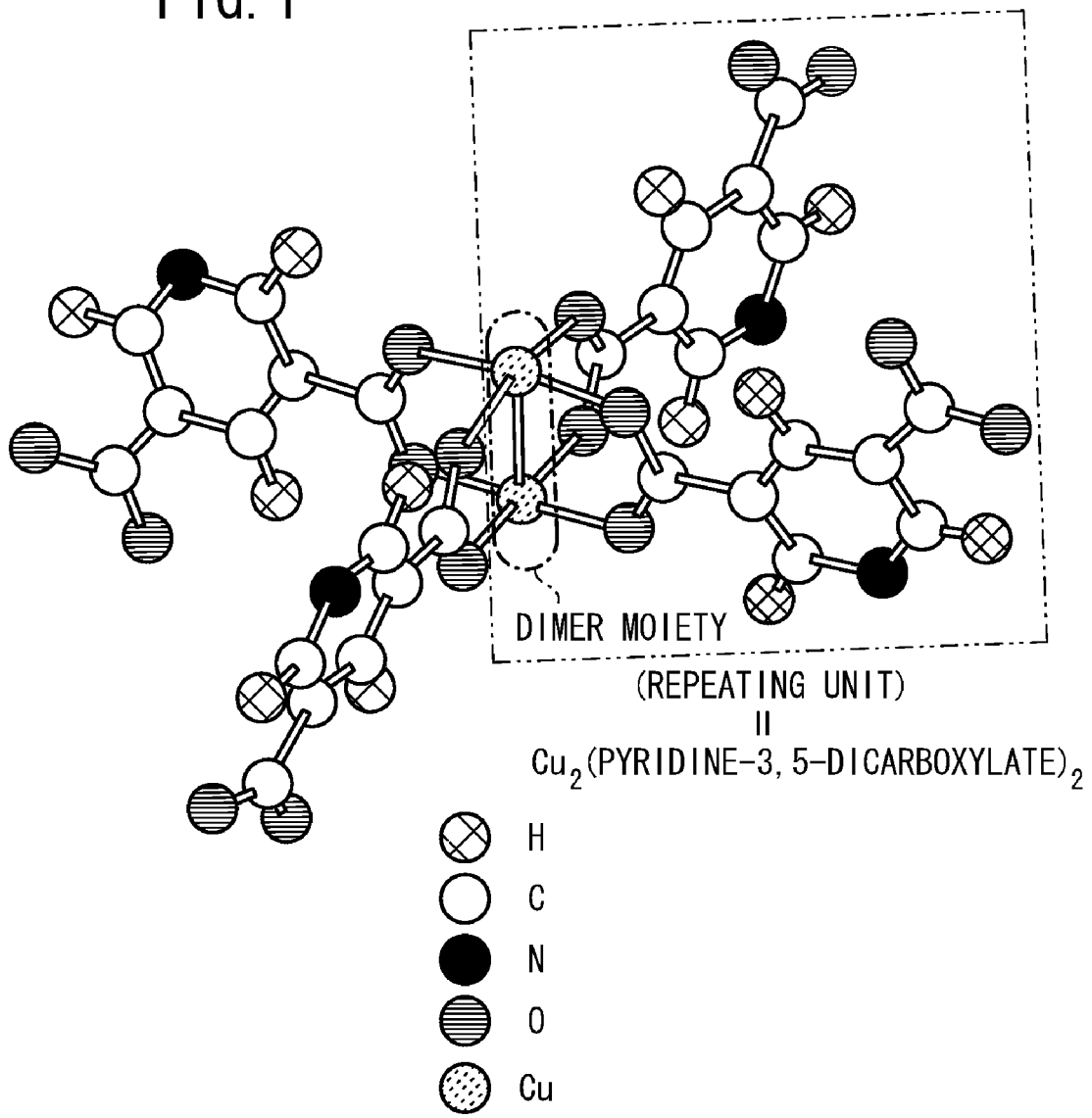
FIG. 1 is a schematic stereoscopic view showing a structure containing a Cu$_2$(pyridine-3,5-dicarboxylate)$_2$ repeating unit and two pyridine-3,5-dicarboxylate groups bonded thereto.

A structure containing the Cu$_2$(pyridine-3,5-dicarboxylate)$_2$ repeating unit and two pyridine-3,5-dicarboxylate groups bonded thereto is shown in FIG. 1. In this structure, a portion surrounded by the two-dot chain line is the repeating unit. All conjugate bonds of the pyridine rings, etc. are omitted in FIG. 1 as a matter of convenience for explanation, as well as in the other drawings.

Figure 2:
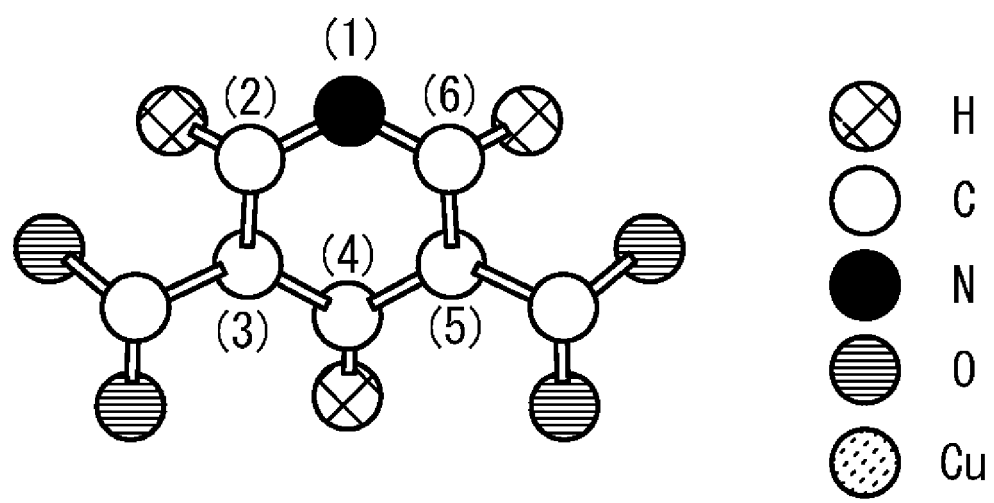
FIG. 2 is a schematic plan view showing the pyridine-3,5-dicarboxylate group.

The structure of the pyridine-3,5-dicarboxylate group will be described below referring to FIG. 2. The structure is planarly shown in FIG. 2. As shown in FIG. 2, the pyridine-3,5-dicarboxylate group contains a pyridine ring and carboxylate groups (—COO) bonded to the 3- and 5-positions thereof. Hydrogen atoms are bonded to the carbon atoms in the 2-, 4-, and 6-positions.

As shown in the portion surrounded by the two-dot chain line in FIG. 1, in the repeating unit, two Cu atoms form a Cu dimer moiety, and two pyridine-3,5-dicarboxylate groups are bonded to the two Cu atoms forming the dimer moiety.

The pyridine-3,5-dicarboxylate group has two carboxylate groups, one O atom in one carboxylate group is bonded to one Cu atom, and the other O atom in the one carboxylate group is bonded to the other Cu atom. To the dimer moiety in the repeating unit, one pyridine-3,5-dicarboxylate group in another repeating unit and one pyridine-3,5-dicarboxylate group in a further repeating unit are bonded in the same manner. Thus, the structure of FIG. 1 is formed.

In other words, the structure of FIG. 1 is such that four pyridine-3,5-dicarboxylate groups are coordinately bonded to one dimer moiety. The four pyridine-3,5-dicarboxylate groups are at an angle of approximately 90° to each other around the Cu—Cu bond axis of the dimer moiety. This coordination structure is hereinafter referred to also as the Cu$_2$(COO)$_4$ paddle-wheel structure.

The other carboxylate group in the pyridine-3,5-dicarboxylate group is coordinately bonded to another dimer moiety (not shown in FIG. 1) in the same manner, to form another Cu$_2$(COO)$_4$ paddle-wheel structure. One Cu atom in the dimer moiety of the Cu$_2$(COO)$_4$ paddle-wheel structure may coordinately bonded to an N atom in a pyridine-3,5-dicarboxylate group of another Cu$_2$(COO)$_4$ paddle-wheel structure, to form a unit cell shown in FIG. 3. In FIG. 3, arrows a, b, and c represent the a-, b-, and c-axes of the unit cell.

The unit cell contains twelve Cu atoms and twelve pyridine-3,5-dicarboxylate groups. Thus, the composition ratio between the Cu atoms and pyridine-3,5-dicarboxylate groups is 1:1. As described above, one dimer moiety and four pyridine-3,5-dicarboxylate groups form the Cu$_2$(COO)$_4$ paddle-wheel structure.

The unit cell has a space group of P6$_3$mc represented by the Hermann-Mauguin notation, and thereby has a hexagonal crystal system. The angle between the a- and b-axes is 120°, and the angle between the b- and c-axes and the angle between the c- and a-axes are 90°. The a- and b-axes have a length of 18.71 to 19.41 Angstroms, and the c-axis has a length of 13.40 to 13.62 Angstroms, measured by instrumental analysis.

Figure 4:
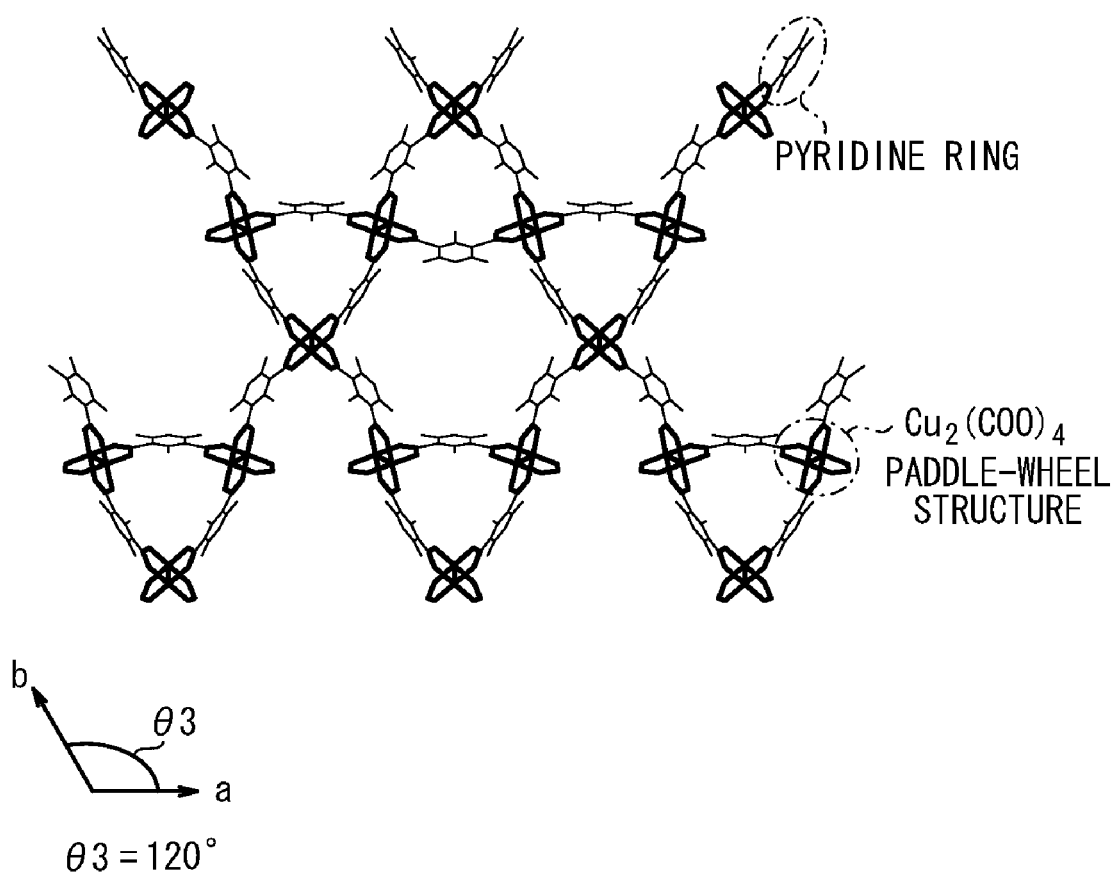
FIG. 4 is a schematic plan view showing a plane containing the a- and b-axes of the unit cell observed in the c-axis direction.

A plane containing the a- and b-axes is shown in FIG. 4. The centers of the dimer moieties are positioned on a straight line parallel to the a-axis, a straight line parallel to the b-axis, or a straight line parallel to the bisector of the angle between the a- and b-axes.

In this plane, two adjacent dimer moieties on the straight line parallel to the b-axis are bonded via the coordinate bonds of the pyridine-3,5-dicarboxylate group. Two adjacent pyridine-3,5-dicarboxylate groups sandwiching the dimer moiety therebetween face each other across a plane perpendicular to the above described plane containing the a- and b-axes. The plane contains the straight line parallel to the b-axis, on which the center of the dimer moiety is positioned. Thus, the two adjacent groups are positioned in opposite regions on the plane.

Figure 5:
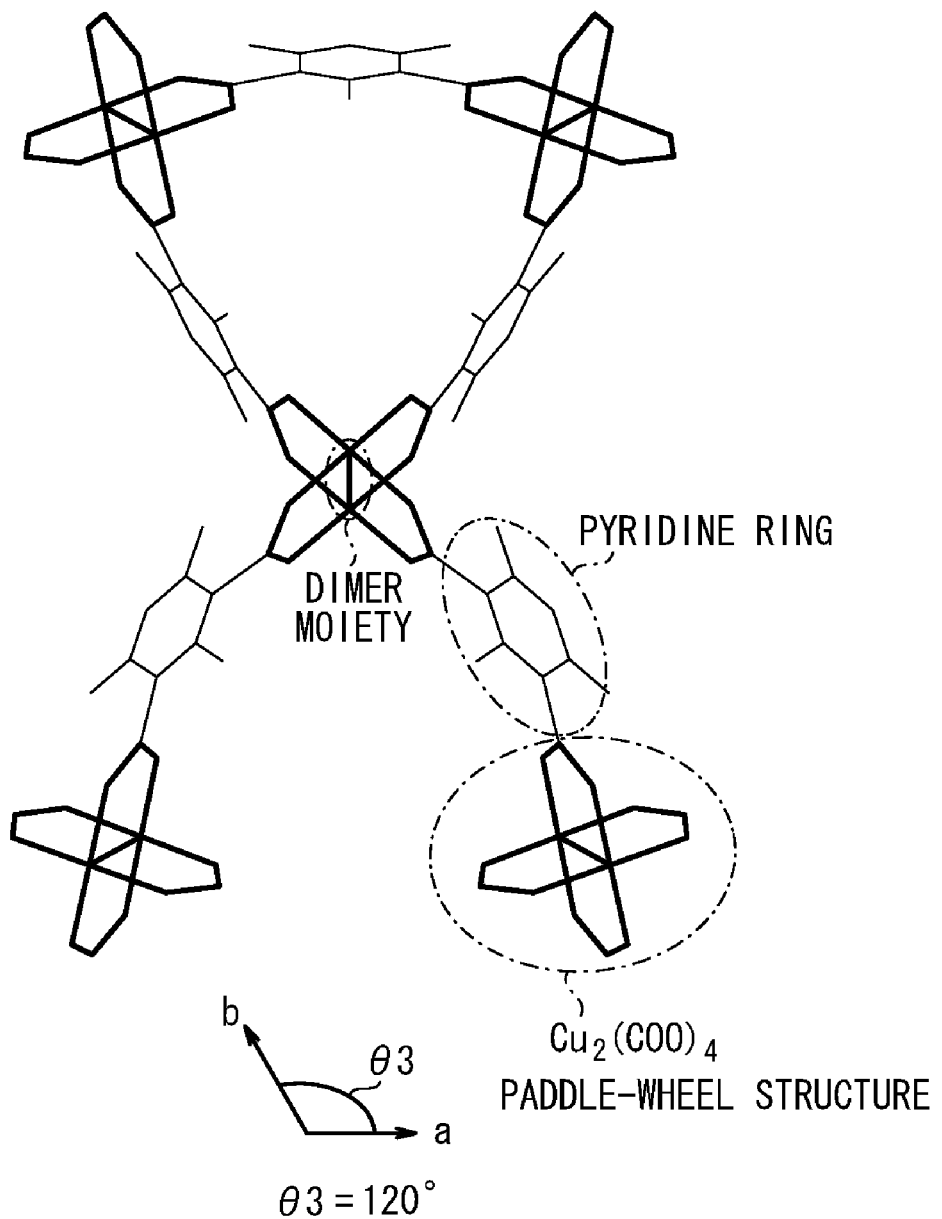
FIG. 5 is a schematic enlarged plan view showing a principal part of the plane of FIG. 4.

As shown in FIG. 5, the two adjacent pyridine-3,5-dicarboxylate groups face each other also across a plane parallel to the above described plane containing the a- and b-axes. Thus, the two adjacent groups are positioned in opposite regions on the plane.

Furthermore, the two adjacent pyridine-3,5-dicarboxylate groups are coordinately bonded to the dimer moiety such that the N atoms in the pyridine rings are the most distant from each other. Specifically, the N atom in the pyridine ring of one pyridine-3,5-dicarboxylate group is in the lowermost position in the c-axis direction, and the N atom in the pyridine ring of the other group is in the uppermost position in the c-axis direction.

As described above, the dimer moieties and the pyridine-3,5-dicarboxylate groups are alternately bonded to form a straight structure in the direction parallel to the b-axis.

The same straight structure is formed in the direction parallel to the a-axis. Thus, two adjacent dimer moieties on the straight line parallel to the a-axis are bonded via the coordinate bonds of the pyridine-3,5-dicarboxylate group, and the dimer moieties and the pyridine-3,5-dicarboxylate groups are alternately bonded to form the straight structure.

Also two adjacent dimer moieties on the straight line parallel to the bisector of the angle between the a- and b-axes are bonded via the coordinate bonds of the pyridine-3,5-dicarboxylate group in the same manner as above. The dimer moieties and the pyridine-3,5-dicarboxylate groups are alternately bonded to form the straight structure also in the direction parallel to the bisector.

As shown in FIG. 4, the $Cu_2(COO)_4$ paddle-wheel structures are positioned only at the intersections X between the straight structures extending parallel to the b-axis and those extending parallel to the a-axis, the intersections Y between those extending parallel to the b-axis and those extending parallel to the bisector of the angle between the a- and b-axes, and the intersections Z between those extending parallel to the a-axis and those extending parallel to the bisector of the angle between the a- and b-axes. Thus, the straight structure extending parallel to the a-axis, the straight structure extending parallel to the b-axis, and the straight structure extending parallel to the bisector of the angle between the a- and b-axes do not intersect at one point.

The intersections X and Y are alternately formed on the straight structure extending parallel to the b-axis. The intersections X and Z are alternately formed on the straight structure extending parallel to the a-axis. Furthermore, the intersections Z and Y are alternately formed on the straight structure extending parallel to the bisector of the angle between the a- and b-axes.

Accordingly, the organometallic complex has a two-dimensional network structure in the plane parallel to the a- and b-axes. The two-dimensional network structure contains the straight structures extending parallel to the b-axis, those extending parallel to the a-axis, and those extending parallel to the bisector of the angle between the a- and b-axes, connected by the $Cu_2(COO)_4$ paddle-wheel structures.

Figure 6:
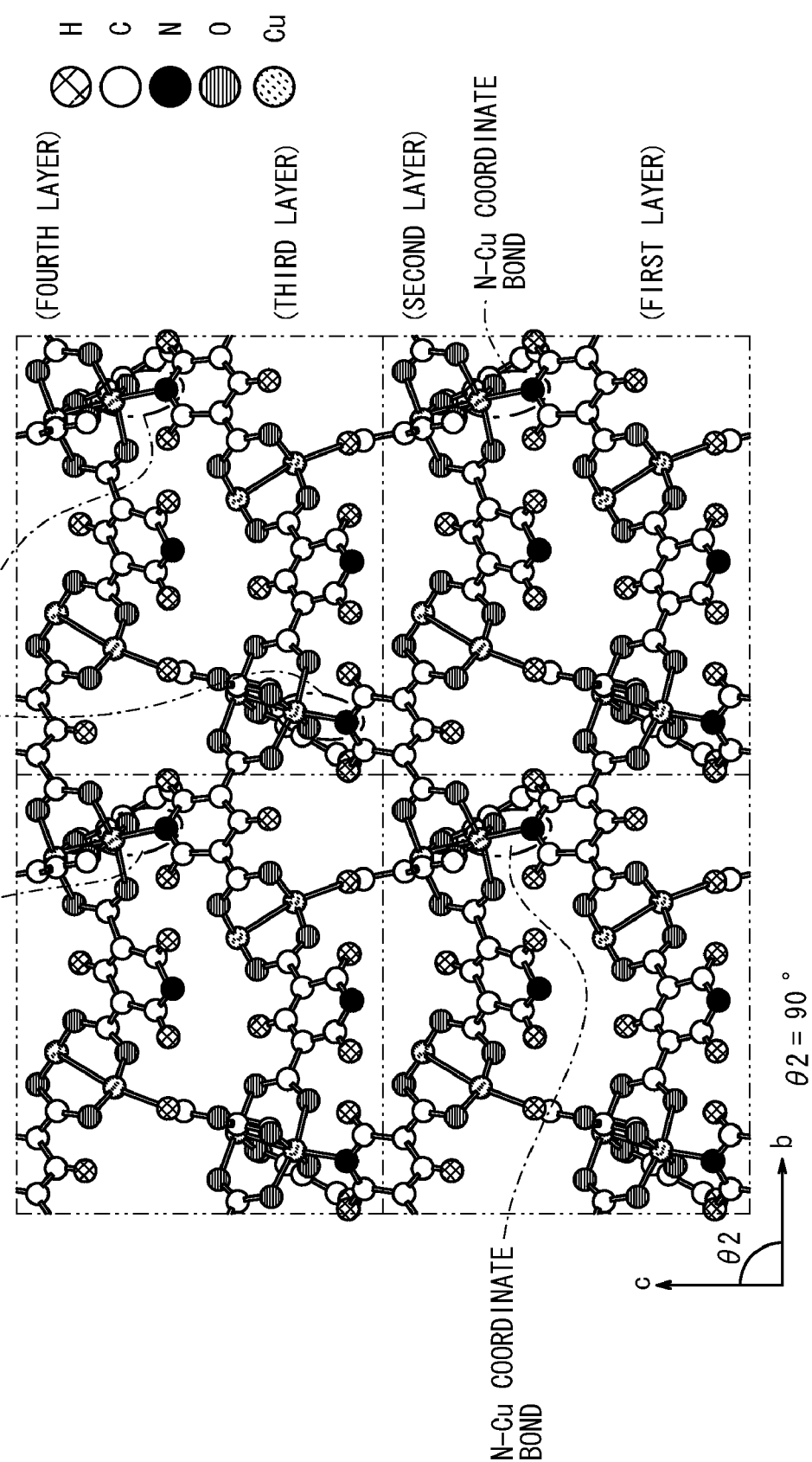
FIG. 6 is a schematic stereoscopic view showing a three-dimensional structure formed by stacking the two-dimensional structures of FIGS. 4 and 5 observed in the a-axis direction.

As shown in FIG. 6 observed in the a-axis direction, the organometallic complex has a three-dimensional structure formed by stacking the above two-dimensional structures in the c-axis direction. In FIG. 6, first, second, third, and fourth layers are stacked in this order from the bottom.

Figure 7:
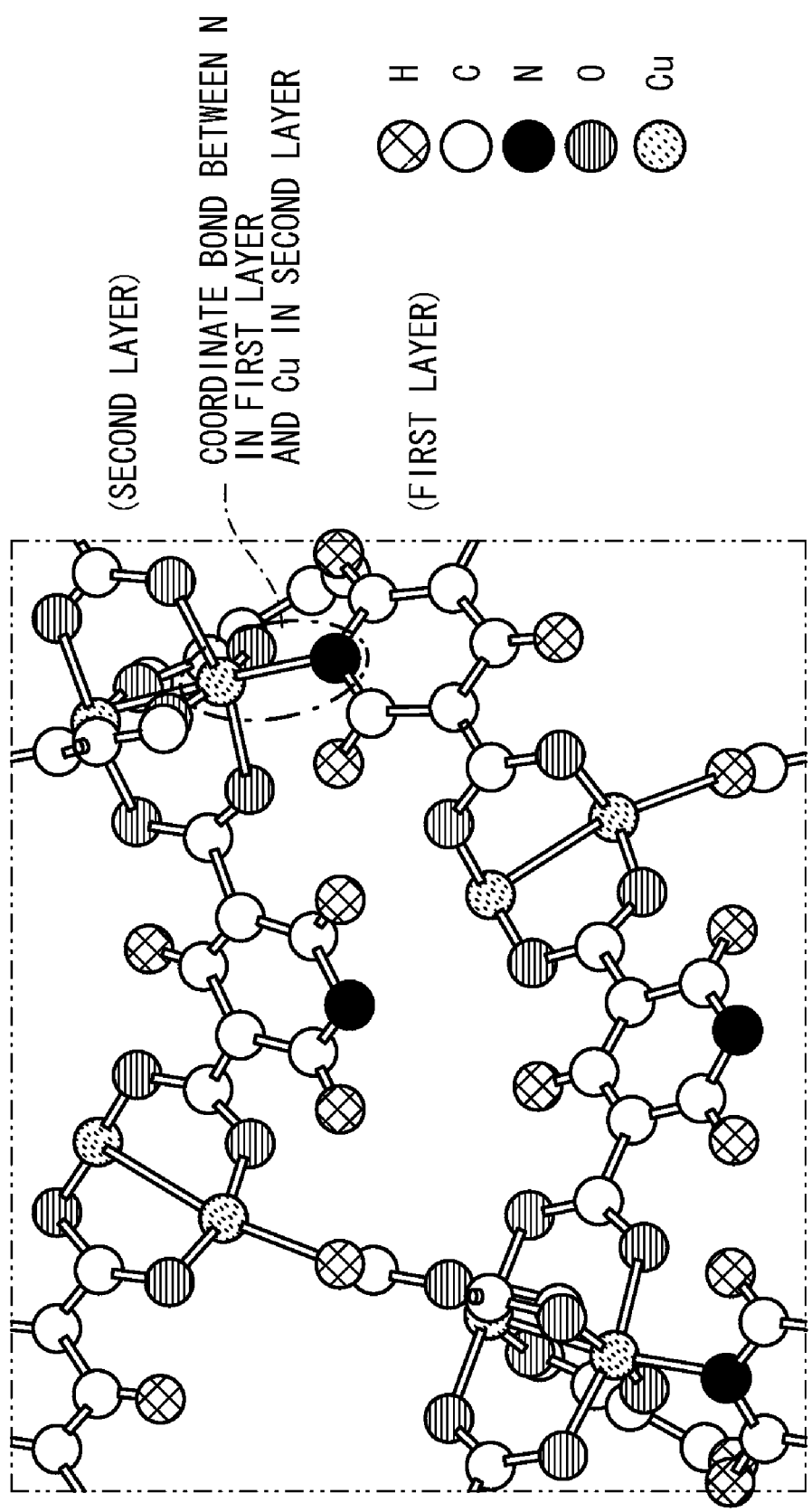
FIG. 7 is an enlarged view showing a principal part of FIG. 6.

FIG. 7 is an enlarged view showing a principal part of FIG. 6. As shown in FIG. 7, the first and second layers are connected such that an N atom (closer to the second layer) in a pyridine ring of a pyridine-3,5-dicarboxylate group in the first layer is coordinately bonded to a Cu atom (closer to the first layer) in a dimer moiety in the second layer. It should be noted that a Cu atom (closer to the second layer) in a dimer moiety in the first layer is not bonded to an N atom (closer to the first layer) in a pyridine ring of a pyridine-3,5-dicarboxylate group in the second layer.

Also the second and third layers are connected such that an N atom (closer to the third layer) in a pyridine ring of a pyridine-3,5-dicarboxylate group in the second layer is coordinately bonded to a Cu atom (closer to the second layer) in a dimer moiety in the third layer.

Also the third and fourth layers are connected in the same manner as the first and second layers. The positions of the N—Cu coordinate bonds between the third and fourth layers correspond to those between the first and second layers.

When a fifth layer is stacked on the fourth layer, the fourth and fifth layers are connected in the same manner as the second and third layers. As is clear from this, in the three-dimensional layer structure, the connection between the first and second layers is repeated in the c-axis direction.

Figure 8:
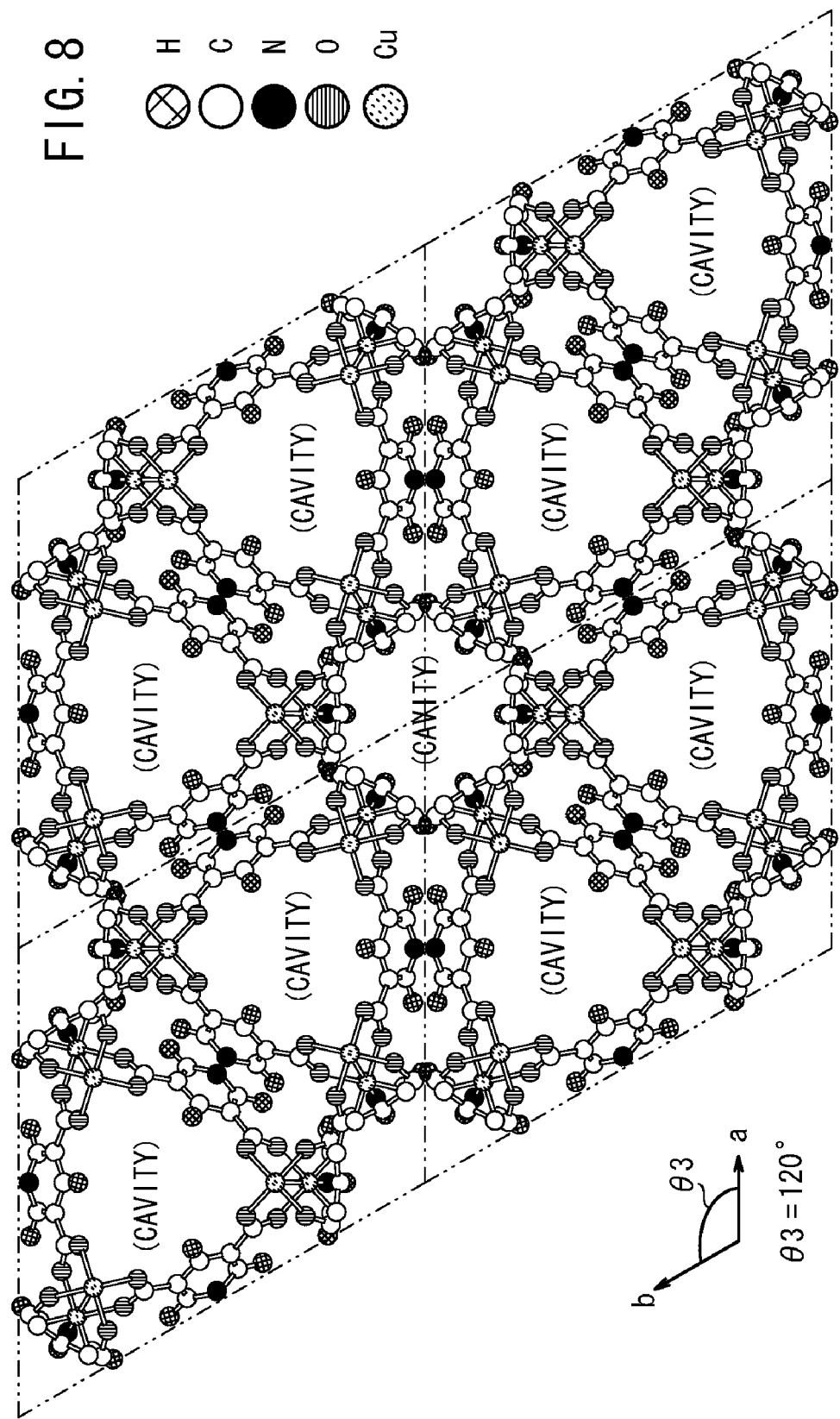
FIG. 8 is a schematic plan view showing the three-dimensional structure of FIG. 6 observed in the c-axis direction.
Figure 9:
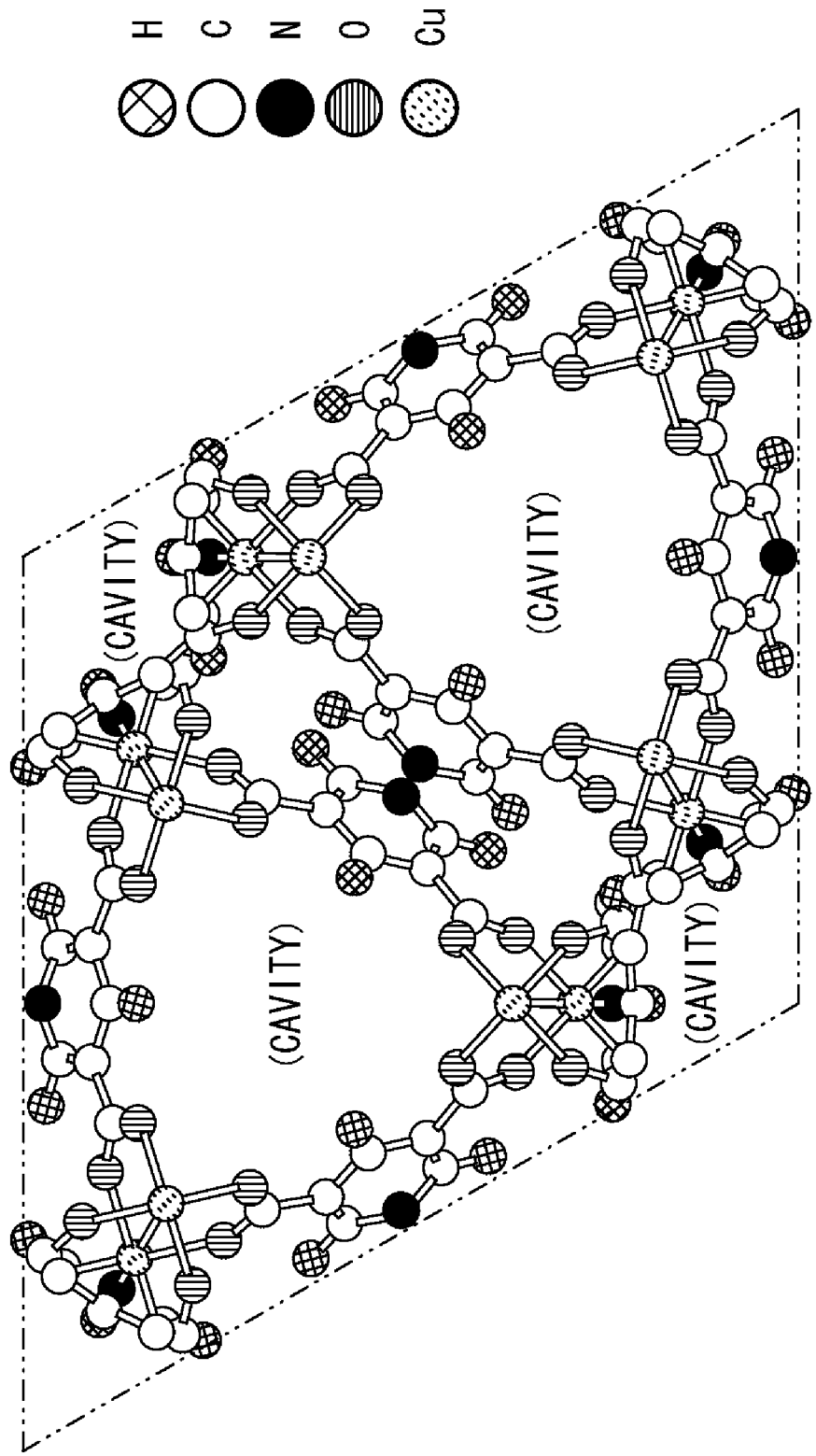
FIG. 9 is an enlarged view showing a principal part of FIG. 8.

FIG. 8 is a plan view showing the layer structure observed in the c-axis direction. As shown in FIG. 8, the organometallic complex has a plurality of cavities (spaces), which are not densely filled with atoms, in the plane containing the a- and b-axes. The cavity has a pore shape with an opening diameter and inner diameter of several Angstroms. FIG. 9 is an enlarged view showing a principal part of FIG. 8. As shown in FIG. 9, the Cu, O, and N atoms are exposed to the cavity in the inner wall of the cavity.

The cavity (the pore-shaped space), which has the opening diameter and inner diameter of several Angstroms, is sufficient in size for introducing and releasing hydrogen molecules. The Cu, O, and N atoms exposed to the cavity in the inner wall of the cavity act as hydrogen molecule adsorption sites effectively. Thus, the organometallic complex can store and release a large amount of hydrogen depending on the increase and decrease of ambient hydrogen pressure even at approximately room temperature.

When the organometallic complex having the above structure is subjected to an X-ray diffraction measurement within a diffraction angle 2θ range of 5° to 20°, peaks are found at 5.2-5.5, 8.33-8.63, 9.17-9.47, 10.55-10.95, 12.41-12.81, 13.03-13.33, 14.10-14.44, 15.56-15.76, 15.93-16.43, 16.85-17.25, 17.23-17.73, 18.49-18.99, and 19.27-19.77 degrees.

A method for producing the organometallic complex [$Cu_2$(pyridine-3,5-dicarboxylate)$_2$]$_n$ will be described below. In this embodiment, the method contains a first step of dissolving starting materials to prepare a solution, a second step of adding a crystallinity improver to the solution, a third step of heating the solution to obtain a reaction product from the starting materials, and a fourth step of removing guest molecules from the reaction product.

In the first step, the starting materials are dissolved in a solvent.

A copper carboxylate salt and pyridine-3,5-dicarboxylic acid are selected as the starting materials. Specifically, the copper carboxylate salt is copper acetate monohydrate or copper acetate anhydrate.

The solvent is not limited as long as both of the copper acetate monohydrate or anhydrate and the pyridine-3,5-dicarboxylic acid can be dissolved therein. Preferred examples of such solvents include dimethylformamide, diethylformamide, dimethylsulfoxide, ethanol, and methanol. The dimethylformamide is most preferred from the viewpoint of increasing the crystallinity of the organometallic complex.

The mole ratio of the copper acetate monohydrate or anhydrate to the solvent is preferably 0.01 to 1.0 mol %, more preferably 0.1 to 0.5 mol %. The mole ratio of the pyridine-3,5-dicarboxylic acid to the solvent is preferably 0.01 to 3.0 mol %, more preferably 0.2 to 1.0 mol %.

It is preferred that the mole ratio of the copper acetate monohydrate or anhydrate is lower than that of the pyridine-3,5-dicarboxylic acid. In this case, the resultant organometallic complex can exhibit an increased crystallinity.

In the second step, the crystallinity improver for increasing the crystallinity of the organometallic complex is added to the solution containing the starting materials dissolved. Specifically, the crystallinity improver is acetic acid or formic acid.

The satisfactory mole ratio of the acetic acid to the solvent is 0.0001 to 0.5 mol %, and that of the formic acid is 0.0001 to 0.1 mol %. The mole ratio of the acetic acid is more preferably 0.001 to 0.1 mol %, and that of the formic acid is more preferably 0.001 to 0.05 mol %. The crystallinity of the final product organometallic complex can be significantly improved only by using the crystallinity improver even with such a small amount.

The solution is added to an airtight container, and the container is closed. Then, in the third step, the airtight container containing the solution is heated at a temperature of 50° C. to 140° C. for a time of 24 to 168 hours. When the heating is carried out at lower than 50° C. or for less than 24 hours, the copper acetate monohydrate or anhydrate and the pyridine-3,5-dicarboxylic acid are not sufficiently reacted, resulting in a poor reaction product yield. On the other hand, the heating at higher than 140° C. for more than 168 hours is not economical because the reaction rate and yield can be sufficiently improved even under milder heating conditions. In the third step, the heating is further preferably carried out at a temperature of 70° C. to 90° C. for a time of 60 to 120 hours.

The copper acetate monohydrate or anhydrate is reacted with the pyridine-3,5-dicarboxylic acid by the heating, whereby the $[Cu_2(pyridine-3,5-dicarboxylate)_2]_n$ complex is generated with high crystallinity. The heating method is not particularly limited. Specifically, for example, the solution is preferably heated by a sand bath.

The obtained $[Cu_2(pyridine-3,5-dicarboxylate)_2]_n$ reaction product contains the guest molecules such as solvent molecules and water molecules in the above described cavities (the pore-shaped spaces), etc. Therefore, in the fourth step, a guest removal treatment is carried out to remove the guest molecules.

A guest removal treatment for removing the solvent molecules may be carried out as follows. First, the crystal surfaces of the obtained $[Cu_2(pyridine-3,5-dicarboxylate)_2]_n$ complex are washed with the above described solvent. Then, the unreacted starting materials (i.e. the copper acetate monohydrate or anhydrate and the pyridine-3,5-dicarboxylic acid) are dissolved in the solvent and removed from the crystal surfaces.

The washed $[Cu_2(pyridine-3,5-dicarboxylate)_2]_n$ crystal is immersed in a dry chloroform, so that the solvent molecules in the cavity, etc. are replaced with the dry chloroform molecules.

The reaction product is left in the dry chloroform overnight, the dry chloroform is changed with a new one, and is further left therein for one week while changing the dry chloroform. As a result, approximately all the solvent molecules are replaced with the dry chloroform molecules. The dry chloroform may be changed 1 to 10 times in the one week. The replacement can be performed more reliably when the dry chloroform is changed more frequently. Therefore, the dry chloroform is preferably changed at least 5 times in the one week.

After the guest removal treatment for removing the solvent molecules is completed, another guest removal treatment is carried out to remove the water molecules and dry chloroform molecules. Specifically, the organometallic complex is isolated from the dry chloroform by filtration, and is subjected to a heating treatment under a reduced pressure.

The heating treatment is preferably carried out under a high vacuum pressure of 0.013 Pa or less. Such a high vacuum atmosphere may be achieved by using a turbomolecular pump, etc.

The heating temperature used in the heating treatment is preferably 40° C. to 300° C., more preferably 80° C. to 200° C. The temperature is preferably risen at a low rate of about 1° C./minute.

The heating treatment is carried out under the reduced pressure for 1 to 7 days to remove the water and dry chloroform molecules, whereby the $[Cu_2(pyridine-3,5-dicarboxylate)_2]_n$ crystal is obtained with high purity.

When the obtained $[Cu_2(pyridine-3,5-dicarboxylate)_2]_n$ is left in air after the guest removal treatment, the organometallic complex tends to be deactivated due to water adsorption. Therefore, it is preferred that the complex is stored in an inert gas atmosphere such as an argon atmosphere.

Though the acetic or formic acid is added to the solution containing the starting materials in the embodiment, the third and fourth steps may be carried out without the addition (i.e. without the second step). The $Cu_2(pyridine-3,5-dicarboxylate)_2]_n$ can be produced also in this case.

Example 1

The present invention will be described in detail below referring to Examples without intention of restricting the scope of the present invention.

56.7 mg of copper acetate monohydrate was added to and dissolved in 9.89 ml of dimethylformamide, and 65.3 mg of pyridine-3,5-dicarboxylic acid was added to and dissolved in the solution. Then, 0.11 ml of acetic acid was further added thereto, and the resultant was sufficiently stirred.

The obtained solution was added to a 20-ml-volume vial. The vial was embedded in a sand bath and left therein at 70° C. for 90 hours to generate $[Cu_2(pyridine-3,5-dicarboxylate)_2]_n$ crystals.

The procedures were repeated 30 times, whereby total approximately 1 g of the crystalline $[Cu_2(pyridine-3,5-dicarboxylate)_2]_n$ was obtained.

0.05 g of the crystalline $[Cu_2(pyridine-3,5-dicarboxylate)_2]_n$ was weighed and washed with 50 ml of a dry dimethylformamide. The washed complex was immersed in a dry chloroform. After the crystalline was left therein overnight, the dry chloroform was changed with a new one. Then, the dry chloroform was changed every 24 hours.

The crystalline complex was isolated from the dry chloroform by filtration, and placed in a vessel for a vacuum heating treatment. The inner pressure of the vessel was reduced to a high vacuum pressure of 0.013 Pa or less using a turbomolecular pump. Meanwhile, the vessel was heated at 120° C. for 2 days by a mantle heater.

The vessel was opened in a glove box under an argon atmosphere to collect the complex crystals.

Figure 10:
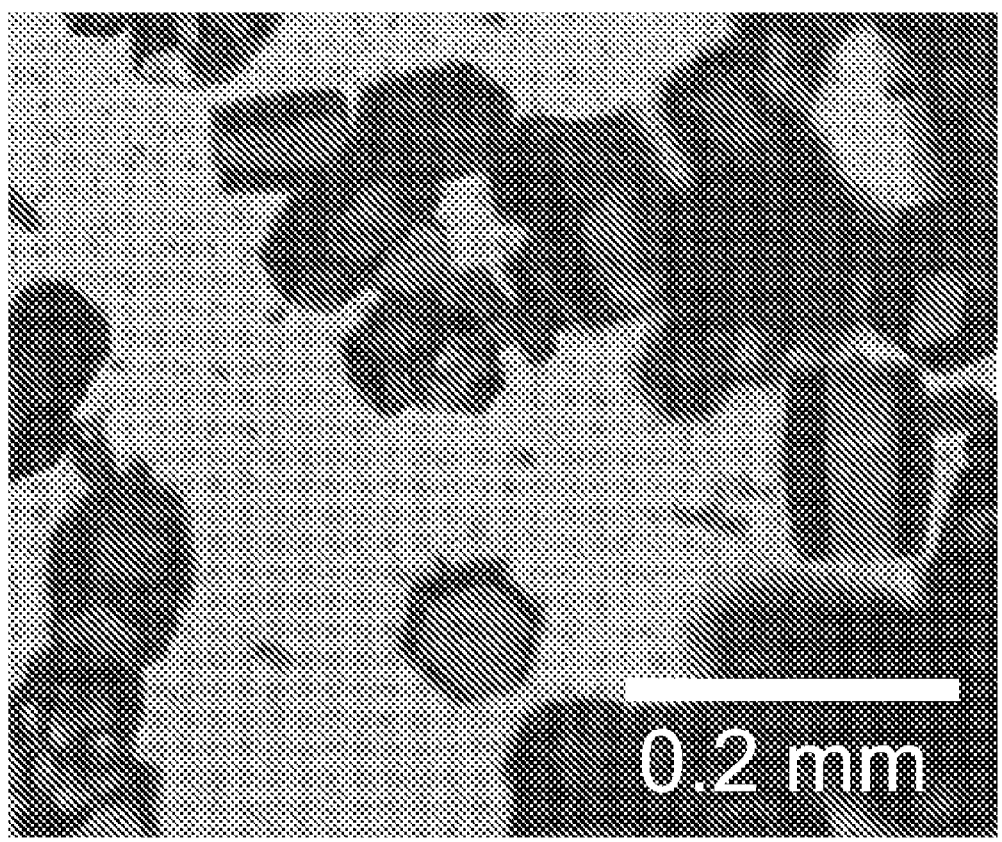
FIG. 10 is an inverted micrograph of crystals taken before a guest removal treatment.
Figure 11:
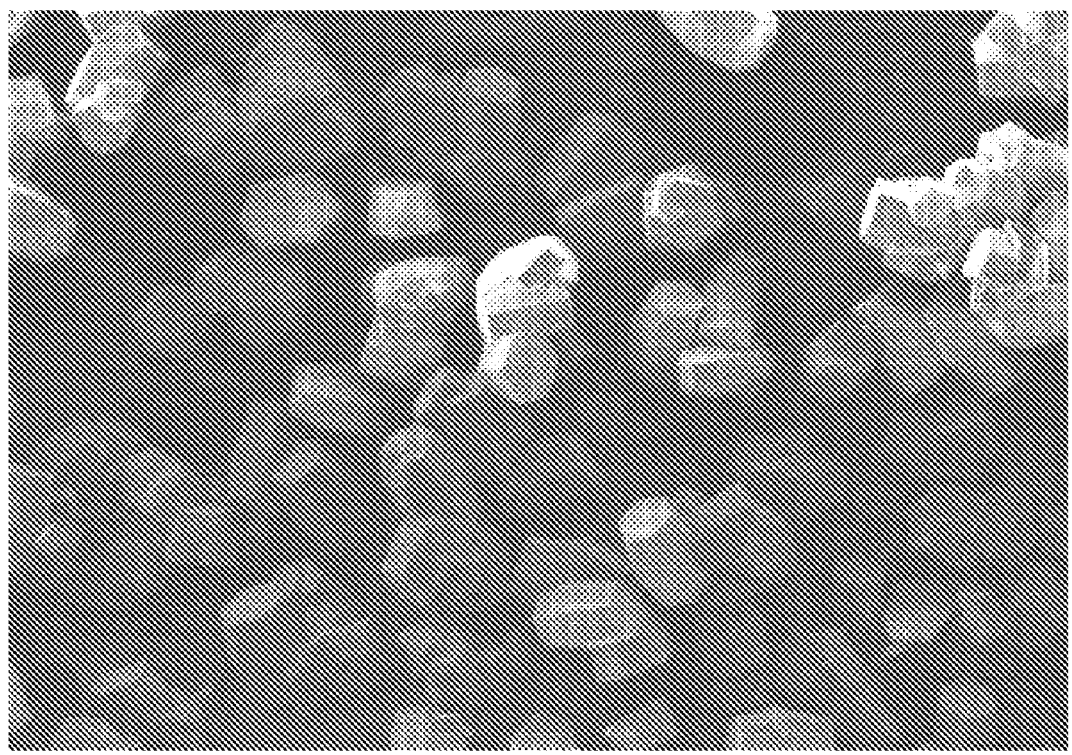
FIG. 11 is a scanning electron micrograph of the crystals taken after the guest removal treatment.

An inverted micrograph of the crystals taken before the guest removal treatment and a scanning electron micrograph of the crystals taken after the treatment are shown in FIGS. 10 and 11, respectively. As shown in FIGS. 10 and 11, the crystals had a shape of approximately regular hexagonal prism.

The crystal collected after the guest removal treatment was irradiated with a monochromatic X-ray beam having a constant wavelength, and the direction and intensity of the X-ray diffraction were measured to determine the crystal structure. As a result, the crystal was judged to have the three-dimensional structure formed by stacking the two-dimensional structures shown in FIGS. 4 and 5. In the determination, RAXIS-RAPID manufactured by Rigaku Corporation was used, and the measured data was analyzed by a computer.

Furthermore, the crystal collected after the guest removal treatment was subjected to an X-ray diffraction measurement. The measured pattern is shown in the upper part of FIG. 12. In this example, peaks were observed at diffraction angles 2θ of 5.2-5.5, 8.33-8.63, 9.17-9.47, 10.55-10.95, 12.41-12.81, 13.03-13.33, 14.10-14.44, 15.56-15.76, 15.93-16.43, 16.85-17.25, 17.23-17.73, 18.49-18.99, and 19.27-19.77 degrees.

Figure 12:
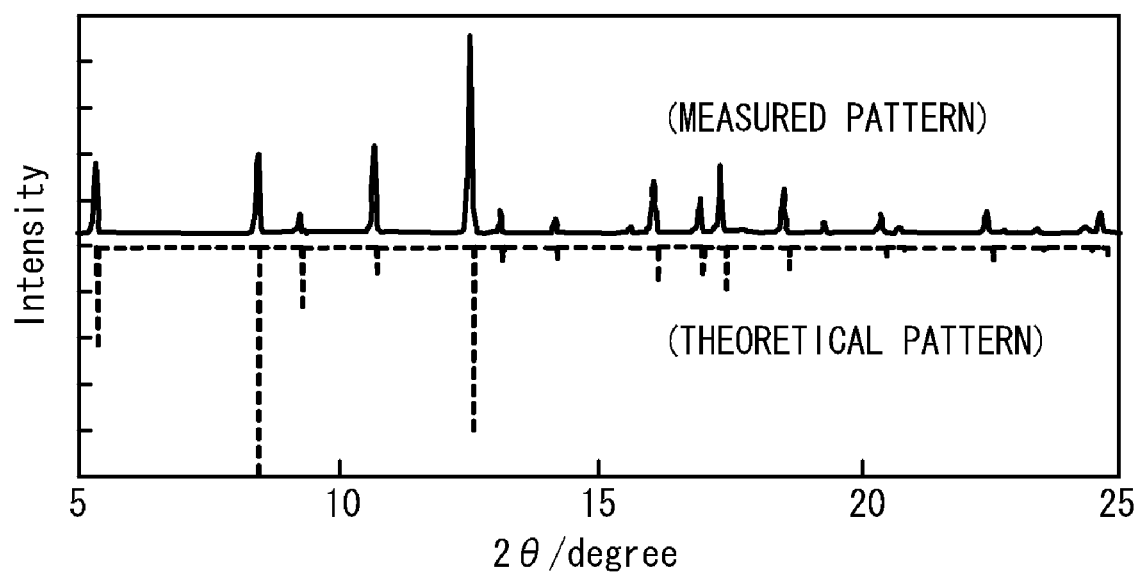
FIG. 12 includes a theoretical X-ray diffraction pattern of the [Cu$_2$(pyridine-3,5-dicarboxylate)$_2$]$_n$ complex and a measured X-ray diffraction pattern of the crystals obtained after the guest removal treatment.

The theoretical pattern of the $[Cu_2(pyridine-3,5-dicarboxylate)_2]_n$ complex is shown in the lower part of FIG. 12. In comparison with the theoretical pattern, the measured pattern was almost the same as the theoretical pattern. This result supports that the crystal collected after the guest removal treatment has the three-dimensional structure formed by stacking the two-dimensional structures shown in FIGS. 4 and 5.

0.228 g of the crystalline complex collected after the guest removal treatment was added to a sample cell for a displacement-type hydrogen pressure-composition isothermal chart measurement apparatus, and the temperature of the measurement system was controlled at 25° C. A hydrogen gas was introduced stepwise into the sample cell to increase the inner pressure of the cell to 8.27 MPa. The hydrogen storage amounts of the complex under the intermediate hydrogen pressures were calculated from hydrogen storage equilibrium pressures.

Then, the hydrogen was discharged stepwise to reduce the inner hydrogen pressure of the sample cell to 0.008 MPa. The hydrogen release amounts at the intermediate hydrogen pressures were calculated from hydrogen release equilibrium pressures.

The results are shown in the graph of FIG. 13. In this graph, the weight ratio (% by weight) of the stored hydrogen to the crystalline complex is shown on the horizontal axis, and the hydrogen pressure of the sample cell is shown on the vertical axis.

As shown in FIG. 13, the hydrogen storage amount and the hydrogen release amount of the $[Cu_2(pyridine-3,5-dicarboxylate)_2]_n$ complex were changed depending on the hydrogen pressure. When the hydrogen pressure was 6.5 or 8.27 MPa, the hydrogen storage amount was 0.45% or 0.517% by weight, respectively. The amount values are larger than the hydrogen adsorption amount 0.35% of the above described Cu-BTC measured at the room temperature under a hydrogen pressure of 6.5 MPa, reported in *Advanced Functional Materials*, 16(4), 520-524.

Thus, it is apparent that the $[Cu_2(pyridine-3,5-dicarboxylate)_2]_n$ complex is capable of storing a larger amount of hydrogen around room temperature.

Although certain preferred embodiments of the present invention have been shown and described in detail, it should be understood that various changes and modifications may be made therein without departing from the scope of the appended claims.

What is claimed is:

1. An organometallic complex represented by the formula of $[Cu_2(pyridine-3,5-dicarboxylate)_2]_n$, comprising a plurality of $Cu_2(pyridine-3,5-dicarboxylate)_2$ repeating units bonded to each other.

2. An organometallic complex according to claim 1, wherein four pyridine-3,5-dicarboxylate groups are coordinately bonded to one Cu dimer moiety, and two adjacent Cu dimer moieties are bonded via one pyridine-3,5-dicarboxylate group.

3. An organometallic complex according to claim 1, wherein the complex is a layer compound formed by stacking two-dimensional structures comprising the $Cu_2(pyridine-3,5-dicarboxylate)_2$ repeating units two-dimensionally bonded to each other.

4. An organometallic complex according to claim 3, wherein the complex has a unit cell containing twelve Cu atoms and twelve pyridine-3,5-dicarboxylate groups, and the unit cell has a space group of $P6_3mc$ in the Hermann-Mauguin notation.

5. An organometallic complex according to claim 1, wherein the complex has a cavity surrounded by a plurality of Cu dimer moieties and a plurality of pyridine-3,5-dicarboxylate groups.

6. An organometallic complex according to claim 5, wherein the complex is capable of storing hydrogen in the cavity.

7. A method for producing an organometallic complex represented by a formula of $[Cu_2(pyridine-3,5-dicarboxylate)_2]_n$, comprising a plurality of $Cu_2(pyridine-3,5-dicarboxylate)_2$ repeating units bonded to each other, wherein the method comprises the steps of
dissolving copper acetate monohydrate or copper acetate anhydrate and pyridine-3,5-dicarboxylic acid in a solvent to prepare a solution,
heating the solution at 50° C. to 140° C. for 24 to 168 hours to obtain a reaction product from the copper acetate monohydrate or anhydrate and the pyridine-3,5-dicarboxylic acid, and
removing a guest molecule from the reaction product.

8. A method according to claim 7, further comprising the step of adding acetic acid or formic acid to the solution.

9. A method according to claim 7, wherein
the step of removing the guest molecule from the reaction product contains:
washing the reaction product with a solvent,
immersing the washed reaction product in a dry chloroform to replace a molecule of the solvent contained in the reaction product with a molecule of the dry chloroform,
isolating the reaction product from the dry chloroform, and
subjecting the reaction product to a heating treatment under a reduced pressure.

10. A method according to claim 9, wherein the immersion of the reaction product in the dry chloroform is continued for one week while changing the dry chloroform.

11. A method according to claim 10, wherein the dry chloroform is changed 1 to 10 times in the one week.

12. A method according to claim 11, wherein the dry chloroform is changed 5 times or more in the one week.

13. A method according to claim 9, wherein the heating treatment of the reaction product is carried out under a reduced pressure of 0.013 Pa or less at a temperature of 40° C. to 300° C.

14. A method according to claim 13, wherein the heating treatment of the reaction product is carried out under the reduced pressure for 1 to 7 days.

* * * * *